United States Patent [19]
Younes

[11] Patent Number: 5,884,622
[45] Date of Patent: Mar. 23, 1999

[54] AUTOMATIC DETERMINATION OF PASSIVE ELASTIC AND RESISTIVE PROPERTIES OF THE RESPIRATORY SYSTEM DURING ASSISTED MECHANICAL VENTILATION

[75] Inventor: Magdy Younes, Winnipeg, Canada

[73] Assignee: University of Manitoba, Winnipeg, Canada

[21] Appl. No.: 771,216

[22] Filed: Dec. 20, 1996

[51] Int. Cl.[6] .................................................. A61M 16/00
[52] U.S. Cl. ................................ 128/204.21; 128/204.23
[58] Field of Search ........................ 128/204.18, 204.21, 128/204.23

[56] References Cited

U.S. PATENT DOCUMENTS

Re. 35,295   7/1996   Estes et al. ......................... 128/204.23
5,107,830    4/1992   Younes ................................ 128/204.18
5,390,666    2/1995   Kimm et al. ........................ 128/204.26
5,572,993   11/1996   Kurome et al. ..................... 128/204.23
5,632,269    5/1997   Zdrojkowski ....................... 128/204.23
5,692,497   12/1997   Schnitzer et al. .................. 128/204.21
5,720,278    2/1998   Lachmann et al. ................ 128/204.23

Primary Examiner—Aaron J. Lewis
Attorney, Agent, or Firm—Sim & McBurney

[57] ABSTRACT

Passive elastic and resistance values for a particular patient are estimated during proportional assist ventilation and other forms of assisted ventilation to permit reliable adjustment for volume-related and flow-related assist gains to meet continuously varying patient muscle pressure. Independent but simultaneous procedures are effected to determine the respective values. The pressure-volume relationship is determined by a modification of the inspiratory hold technique while the pressure-flow relationship is determined by deliberately introducing brief perturbations in pressure, flow and volume and observing the effects obtained.

31 Claims, 4 Drawing Sheets

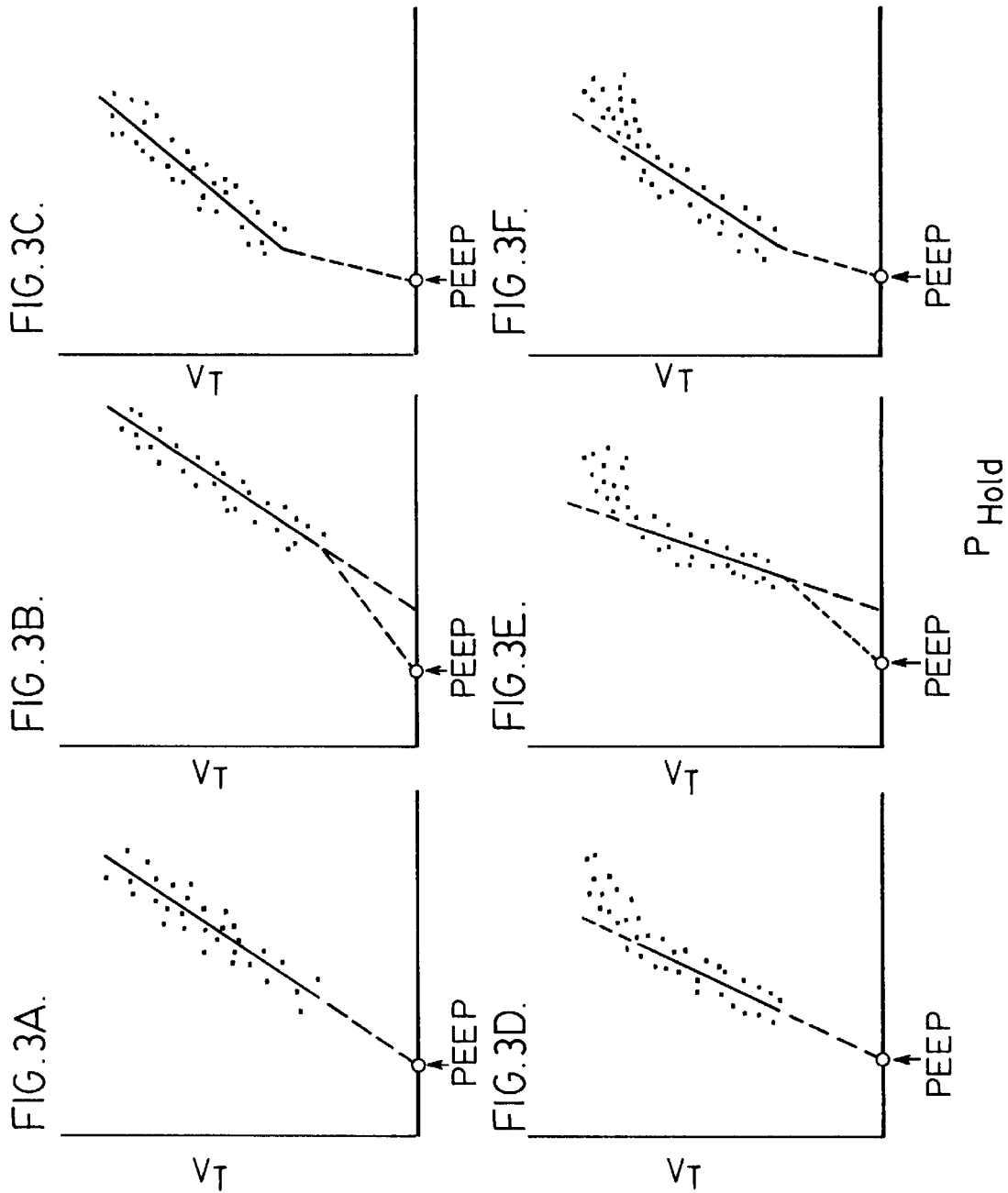

AUTOMATIC DETERMINATION OF PASSIVE ELASTIC AND RESISTIVE PROPERTIES OF THE RESPIRATORY SYSTEM DURING ASSISTED MECHANICAL VENTILATION

FIELD OF THE INVENTION

The present invention relates to ventilation and, in particular, to assisted modes of ventilation.

BACKGROUND TO THE INVENTION

Determination of elastic and resistive properties of the respiratory system is of considerable importance in monitoring disease progression regardless of ventilator mode used. In the proportional assist mode of ventilation, knowledge of these properties is, in addition, essential for proper adjustment of the volume-related and flow-related assist gains. The proportional assist mode of ventilation (PAV®) is fully described in U.S. Pat. No. 5,107,830 (Younes), the disclosure of which is incorporated herein by reference.

Briefly, in proportional assist ventilation, the pressure delivered by the ventilator increases in direct proportion to patient effort and the proportionality applies from breath to breath as well as continuously throughout each inspiration. Proportional assist ventilation operates on the principle that the inspiratory flow ($\dot{V}$) and its integral, volume (V) of a patient contain the necessary information to substantially match the profile of patient effort. By continuously measuring the instantaneous values of flow and volume and applying a gain factor appropriate to each (for flow, cmH$_2$O/L/S and for volume cmH$_2$O/ml), the ventilator can deliver a pressure profile to the patient that amplifies the instantaneous pressure generated in the patient.

The pressure assist provided to the patient may be expressed by the relationship:

$$P_{vent}=K_1 V+K_2 \dot{V}$$

where P$_{vent}$ is the magnitude of the pressure assist, K$_1$ is a gain factor applied to a variable ongoing volume signal (V) and K$_2$ is a gain factor applied to a variable ongoing flow signal ($\dot{V}$). The K$_1$ (or VA) and K$_2$ (or PA) values are fractions of respiratory elastance and respiratory resistance respectively.

In apneic patients, the ventilator provides the only distending force, as reflected by airway pressure (P$_{aw}$). Because P$_{aw}$ provides the total distending pressure, it is possible to reliably determine the elastic and resistive properties of such patients. A variety of reliable methods have been described in the literature for this purpose.

The situation is much more complex in the assist modes of ventilation where ventilator cycle is synchronized with patient's inspiratory effort. In this case, P$_{aw}$ is not the only distending force. Rather, flow ($\dot{V}$) and volume (V) are generated as a result of the combined action of the ventilator (as reflected by P$_{aw}$) and the patient (as expressed in muscle pressure (P$_{mus}$)). To the extent that the magnitude of P$_{mus}$ is continuously varying and cannot be measured or estimated without prior knowledge of patient mechanics, it is not possible to estimate total applied pressure (i.e. P$_{aw}$+P$_{mus}$) at any instant of the inspiratory phase of the ventilator cycle. This problem has made it difficult to reliably estimate mechanical properties in the assist modes.

Given that the behaviours of P$_{aw}$, flow and volume during a "normal" cycle cannot be used to estimate mechanical properties, one is left with the option of causing a perturbation in one of the primary variables (e.g. P$_{aw}$ or $\dot{V}$) and observing the consequences on the other variables. This approach, which has been used successfully in the controlled ventilation modes, is fraught with difficulties in the assist modes, since the perturbation produced at the airway may alter the pressure generated by the patient (P$_{mus}$) via at least three mechanisms, namely:

(a) Mechanical perturbations are readily perceived. The patient may react at a behavioural level, altering P$_{mus}$;

b) The change in flow or volume produced by the perturbation may alter P$_{mus}$ reflexly (i.e. independent of perception); and c) The change in flow or volume may alter P$_{mus}$ at a strictly mechanical level via the intrinsic properties of respiratory muscles (force-length and force-velocity relations).

If P$_{mus}$ is altered by the perturbation, then one cannot assume that the change in P$_{aw}$ during the perturbation represents the total change in applied force which, in the assist mode, is given by [▲P$_{aw}$+▲P$_{mus}$]. This relationship, again, makes it impossible to use the relation between P$_{aw}$, $\dot{V}$ and V during the perturbation to estimate patient mechanics, unless it can be assured that the perturbation does not change P$_{mus}$.

SUMMARY OF INVENTION

The methods described in detail below and provided in accordance with the present invention make it possible to circumvent the above difficulties, thereby permitting reliable estimates of passive elastic and resistive properties in the face of continuously varying, and unquantifiable, P$_{mus}$, during the assist mode of ventilation. The procedures employed to estimate the passive pressure-volume relationship and the passive pressure-flow relationship are separate procedures but may be combined, as described in detail below.

In one aspect of the present invention, there is provided a method for estimating a passive pressure-volume relationship of a respiratory system in a patient on mechanical ventilatory support and producing spontaneous respiratory effort (assist mode of ventilation) to guide selection of a volume-assist component of the proportional assist ventilation mode (PAV) which comprises:

a) placing a ventilator in the proportional assist mode of ventilation, using empiric values of elastance and resistance or values of elastance and resistance determined by other conventional methods, for initial adjustment of the volume-related and flow-related assist components of the proportional assist ventilation, b) monitoring airway pressure (P$_{aw}$) and flow ($\dot{V}$) and volume (V) to the patient, c) holding flow at or near zero in selected breaths for a period beyond termination of an inspiratory phase of the ventilation, d) measuring P$_{aw}$ at a point as far away as possible from the onset of the inspiratory hold but sooner than the latency for behavioral respiratory responses to provide P$_{hold}$, e) measuring the tidal volume (V$_T$) of the breaths selected for the inspiratory hold step, f) establishing the relationship between P$_{hold}$ and V$_T$ in said selected breaths to provide a pressure-volume relationship over the V$_T$ range encountered during proportional assist ventilation to permit subsequent adjustment of the volume-related assist for proportional assist ventilation.

In another aspect of the present invention, there is provided a method for estimating the passive pressured-flow relationship of the respiratory system in a patient on mechanical ventilatory support and producing spontaneous respiratory efforts (assist modes of ventilation) to guide selection of a flow-assist component in the proportional assist ventilation (PAV) mode, which comprises:

a) placing a ventilator in the proportional assist ventilation mode using empiric values of elastance and resistance or values of elastance and resistance determined by other conventional methods, for initial adjustment of the volume-related and flow-related assist components of the proportional assist ventilation, b) monitoring airway pressure ($P_{aw}$) and flow ($\dot{V}$) and volume (V) to the patient, c) applying brief perturbations in pressure, flow and volume of at least two different forms to selected breaths, such perturbations occurring at a predetermined time during the inspiratory phase of said selected breaths, d) determining the $P_{aw}$, flow ($\dot{V}$) and volume (V) at predetermined times during the perturbation less than latency for behavioural responses, e) determining the $P_{aw}$, $\dot{V}$ and V at similar times to those used in step (d) in unperturbed breaths, f) averaging the results of a number of each form of perturbation and of unperturbed breaths, and g) utilizing the average values of $P_{aw}$, $\dot{V}$ and V obtained from the different forms of perturbation and from unperturbed breaths to provide the pressure-flow relationship to permit subsequent adjustment of the flow-related assist for proportional assist ventilation.

BRIEF DESCRIPTION OF DRAWINGS

FIG. 3, which comprises graphs a, b, c, d, e and f, shows the graphical relationship of $P_{hold}$ to $V_T$ for a series of collections of observations made herein.

GENERAL DESCRIPTION OF INVENTION

The ability to establish passive elastic and resistance values for a particular patient as provided herein arises from several developments in the field of mechanical ventilation.

Figure 1:
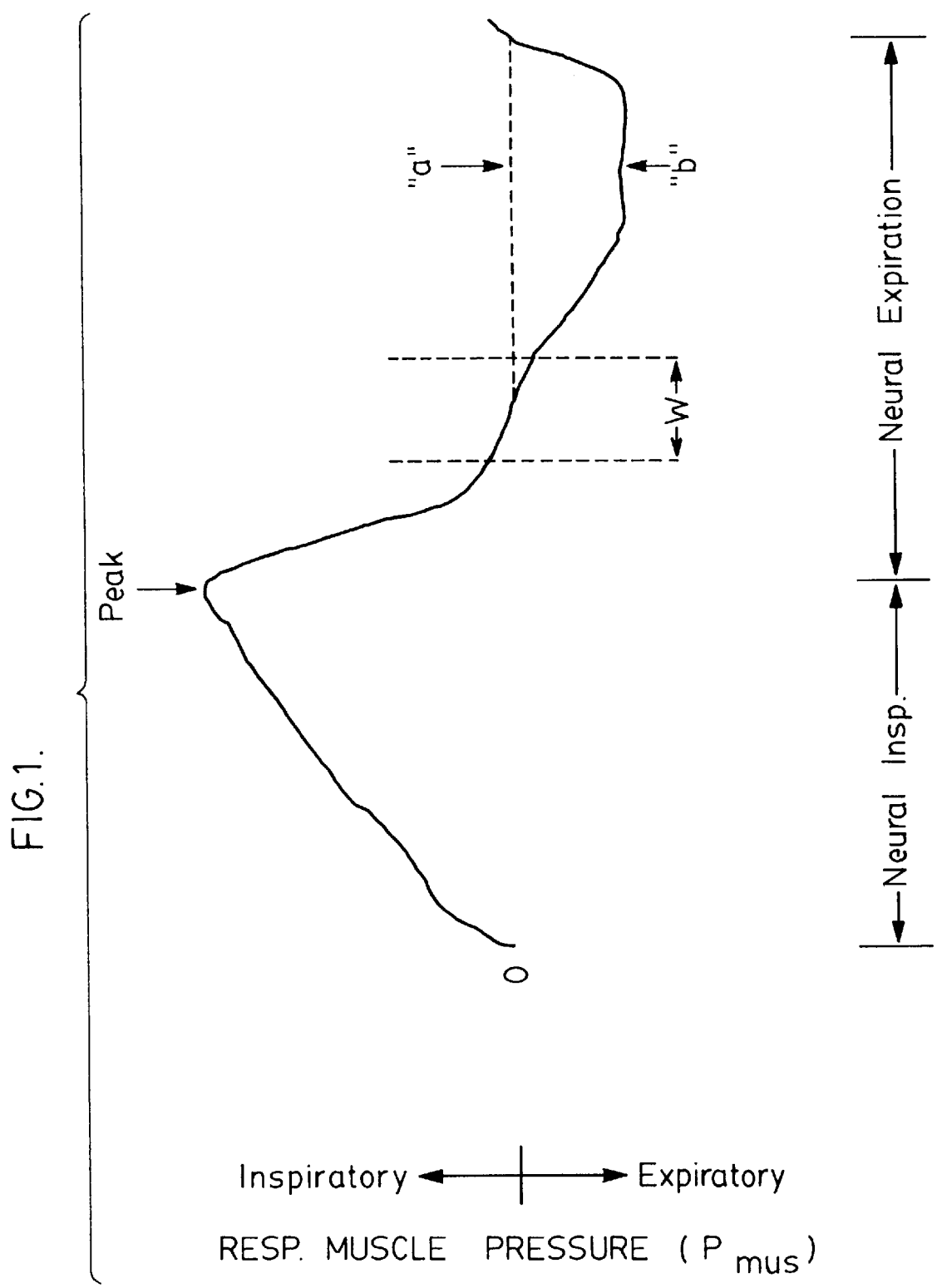
FIG. 1 illustrates the typical pattern of respiratory motor output during a normal respiratory cycle established through decades of investigation in respiratory control.

FIG. 1 illustrates the typical pattern of respiratory motor output during a respiratory cycle as established through decades of investigation in respiratory control. There is a ramp increase in inspiratory muscle activity (or inspiratory $P_{mus}$). After reaching a peak level, the inspiratory output decreases, usually rapidly, towards zero. When the drive to breathe is low, $P_{mus}$ generally stays at zero until the beginning of the next cycle (dashed line "a", FIG. 1).

With a high drive, or with delayed emptying during expiration, expiratory muscles may be recruited. When this happens, the pressure generated by expiratory muscles is minimal early in neural expiration and builds up to a maximum later in expiration (line "b", FIG. 1).

There is, accordingly, a time window (w, FIG. 1), during which $P_{mus}$ is near zero regardless of whether expiratory muscle activity is present or not. Because, in the vicinity of this window, the rate of change in inspiratory or expiratory $P_{mus}$ is relatively small, there is a relative insensitivity to errors in estimating where this window is. Given extensive personal experience of the inventor in monitoring $P_{mus}$ in various conditions, in ventilated patients, "w" should begin within about 200 to about 400 msec of peak inspiratory $P_{mus}$.

The inspiratory hold technique has been in use for many years to measure elastic recoil at end-inspiration both in controlled and assist modes of ventilation. Barring behavioural responses, in the controlled modes (apneic or paralysed patient), the pressure measured during this holding time (plateau pressure) reflects passive elastic recoil. In the assist modes, the plateau pressure is contaminated by an indeterminate amount related to $P_{mus}$, regardless of whether behavioural responses occur.

In the conventional assist modes (volume cycled [assist/control] and pressure cycled [PSV]), there is no linkage between the end of ventilator inspiratory cycle and the end of patient's neural cycle. The inflation phase may terminate at any time during the patient's cycle. The inspiratory hold period may thus coincide with a period during which there is a large inspiratory or expiratory $P_{mus}$.

By contrast, in the proportional assist mode of ventilation (PAV®), the end of the ventilator inflation phase is dictated to occur during the phase of rapid decline in inspiratory $P_{mus}$, very close to "w". If plateau pressure is measured within a few hundred msecs of end of inflation phase, the likelihood of there being significant inspiratory or expiratory $P_{mus}$ is reduced substantially. This phenomenom is employed herein in one aspect of the invention.

The inventor has found that the minimum latency to execute a behavioural response in $P_{mus}$ following a mechanical perturbation at the airway is at least about 200 msec. This is the case even in alert healthy subjects who are prewarned to react as fast as possible to an anticipated intervention. In mechanically ventilated patients, behavioural responses are rarely observed before about 300 msec of a perturbation, even when the patient is awake. This result is related to the usual obtundation and lack of anticipation. It follows that measurements in such patients made within about 300 msec of a mechanical perturbation at the airway are not likely to be subject to errors produced by behavioral responses leading to a change in $P_{mus}$.

The inventor has measured $P_{mus}$ in a large number of subjects in the course of brief (<about 200 msec) perturbations of $P_{aw}$ and flow. The inventor found that the changes in $P_{mus}$ produced by modest changes in $P_{aw}$ or flow (of the magnitude utilized herein) are too small to cause a significant error in estimated mechanical properties. Reflex and mechanical feedback altering $P_{mus}$ in relation to flow and volume are, therefore, not important during perturbations of the kind and magnitude utilized herein.

Although the procedures for estimating the passive elastic (pressure-volume relation) and resistive (pressure-flow relation) are described separately below, they in fact do share common features and requirements and are intended to operate concurrently using a common computer program to provide continuous information on these two properties which is needed for adjustment of the two essential components of PAV, the volume-related and flow-related assist gains.

DESCRIPTION OF PREFERRED EMBODIMENTS

The procedure provided herein now will be described in detail with respect to a preferred embodiments thereof. The invention involves several aspects, as now set forth:

1) Procedure for Automatic Determination of the Passive Elastic Properties (Pressure-Volume Relationship) (first aspect of invention):

In current ventilation practice, elastance ($E_{rs}$) in the assist modes of ventilation is most commonly measured by applying an inspiratory hold, measuring the $P_{aw}$ when a reasonably stable $P_{aw}$ plateau is reached ($P_{plat}$), measuring the corresponding tidal volume ($V_T$) and applying the following equation:

$$E_{rs}=(P_{plat}-\text{PEEP})/V_T$$

where PEEP is the pressure at end-expiration of the ventilation cycle, which is usually above zero in mechanically ventilated patients. Apart from the fact that $P_{plat}$ may be contaminated by inspiratory or expiratory $P_{mus}$, and hence not reflecting passive elastic recoil, the current approach incorporates a serious potential error in that the approach assumes that elastic recoil pressure at the beginning of inspiration (i.e. $P_{EL}EE$) equals PEEP. This is clearly an untenable assumption, since end-expiratory volume (i.e. volume at beginning of inspiratory phase) may be higher than passive functional residual capacity (FRC), due to dynamic hyperinflation, resulting in $P_{EL}EE>\text{PEEP}$, or lower than passive FRC, due to expiratory muscle activity, thereby resulting in $P_{EL}EE<\text{PEEP}$. That these collective errors are serious, is evident from the wide variability in elastance measurements between consecutive determinations and the lack of any good agreement between elastance determination measured in the assist modes using the current approach and determinations made in the same patient after induced passivity and after establishing that the volume at the beginning of the inspiratory phase is, indeed, passive FRC.

In accordance with one embodiment of the invention, these problems are addressed to provide the pressure-volume relationship in the following way:

1) PAV is used as the assist mode of ventilation. In this way, the onset of the inspiratory hold is dictated to coincide with the rapid declining phase of inspiratory $P_{mus}$, close to the point where $P_{mus}$ is near zero.
2) The pressure during the hold is measured at a time less than the latency for behavioural responses, thereby eliminating behavioural responses as a source of contamination of $P_{plat}$, and hence as a source of errors in estimating passive elastance.
3) There is no assumption that elastic recoil at the end of expiration (beginning of inspiration) equals PEEP. Rather, the relationship between $V_T$ and $P_{plat}$, determined according to steps (1) and (2) above, and subsequently referred to as $P_{hold}$, is determined independent of PEEP, taking advantage of the normally wide $V_T$ variability during PAV or, in the absence of spontaneous variability, of deliberate procedures to obtain such a wide range. The intercept of the relation between $V_T$ and $P_{hold}$ may or may not equal PEEP and any differences that may exist provide additional information regarding the difference between end-expiratory volume and passive FRC, or, non-linearities in the pressure-volume relation, both of which are very difficult to obtain otherwise, while being of critical importance in adjusting the volume-related assist in PAV.

The elastance determined according to this approach is different from what is referred to as static elastance, since $P_{aw}$ is measured well before the recommended about 2 to 5 sec of inspiratory hold for determination of true static elastance. $P_{hold}$, and hence elastance estimated by procedure of the invention, overestimates static elastic pressure, and hence static elastance, because viscoelastic pressure may not have completely dissipated at about 200 to 300 msec of the hold manoeuvre.

Although measurements made according to the present invention may not truly reflect static elastic behaviour, they are more appropriate for determining elastic behaviour during the inspiratory phase than any prior art procedure and are, hence, more relevant to adjusting the volume-assist gain of PAV.

Preferred Procedure for Pressure-Volume Relationship:

The patient first is placed in the PAV mode of ventilation. Provision is made for monitoring $P_{aw}$, flow and volume. Initial settings of flow assist (FA) and volume assist (VA) on the ventilator may be based on previously determined values of resistance (R) and elastance (E) in the controlled mode of ventilation. Alternatively, default values for FA and VA may be used. The primary intent of these values is to provide some assist but, at the same time, remain below the patient's resistance (R) and elastance (E), respectively. So long as this relationship is maintained, the end of ventilator inflation phase coincides with the phase of decline in inspiratory $P_{mus}$ (see FIG. 1 and above discussion thereof). Suitable default values may be FA=[endotracheal (ET) tube resistance +4], and VA=10 $cmH_2O/l$. If these initial settings are clearly inadequate for the patient as evident by distress, VA and/or FA may be increased gradually but must remain below values that cause a runaway condition, as described in the aforementioned U.S. Pat. No. 5,107,830.

Beyond these initial settings, elastic properties may be determined according to the following paradigm and VA can subsequently be readjusted in light of its results.

The basic procedure is to implement an inspiratory hold manoeuvre and to measure $P_{aw}$ at a point within about 300 msec from the end of inflation phase. For the reasons discussed above, $P_{aw}$ can be measured beyond this point. However, the farther out one goes, the greater the likelihood of contamination with behavioral responses as well as $P_{exp}$ unrelated to behavioral responses.

To minimize anticipatory responses from the patient, the inspiratory hold manoeuvre preferably should not be applied to every breath but rather in random sequence at an average frequency that would allow there to be obtained a reasonable number of data points (e.g. about 15 to 20) in a reasonable time (e.g. about 5 to 20 min). The frequency of such application may also be decreased when results are fairly stable.

Figure 2A:
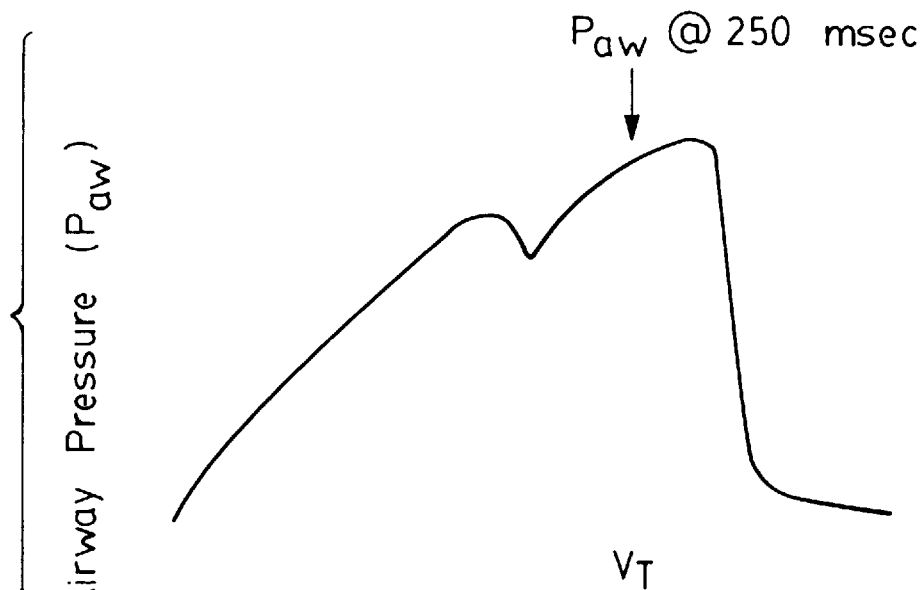
FIG. 2, which comprises graphs A, B and C, contains graphs showing the airway pressure ($P_{aw}$) (Graph A), Volume (Graph B) and Flow (Graph C) during an inspiratory hold manoeuvre as practised, herein in accordance with one embodiment of the invention.
Figure 2B:
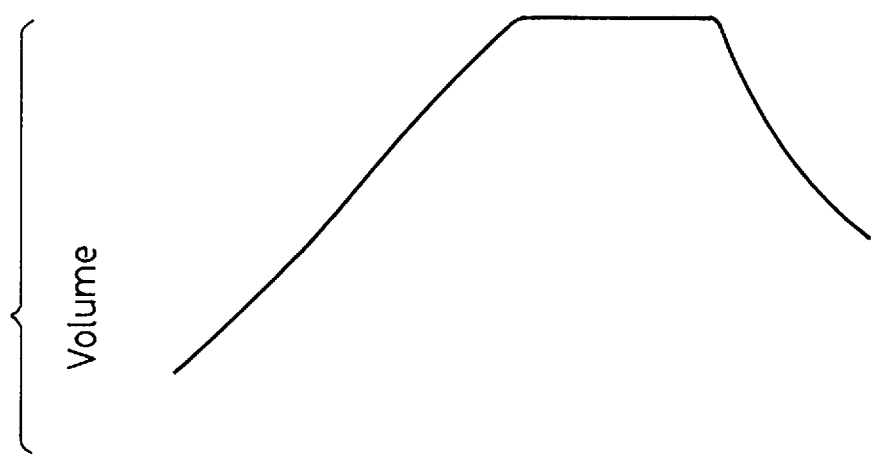
Figure 2C:
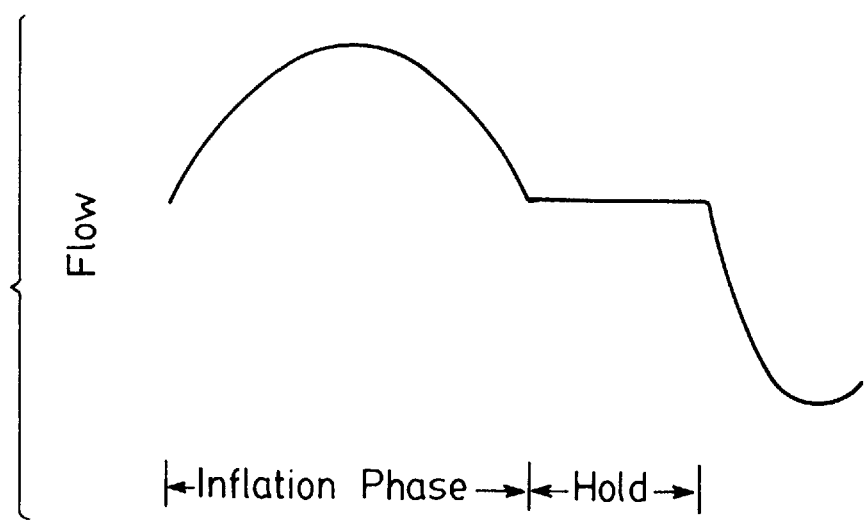

For each inspiratory hold manoeuvre, $P_{aw}$ at about 250 msec from the onset of the inspiratory hold (i.e. zero flow) and the corresponding tidal volume ($V_T$) are noted (see FIG. 2). These data are stored. Ideally, the pressure-volume relation should be defined over a wide $V_T$ range. Patients in the PAV ventilation mode usually display substantial breath by breath variability in $V_T$. This variability tends to be more pronounced in alert patients, and vice versa. In patients with considerable breath by breath variability, inspiratory hold manoeuvres applied randomly produce data at different volumes but there will be greater concentration of data near average $V_T$. The distribution of data points can be made more even through some intelligent paradigms. For example, if there are plenty of data in the average $V_T$ range, breaths with projected low and high $V_T$ may become preferentially targeted for the inspiratory hold manoeuvre. A variety of intelligent algorithms can be entertained which would assist in anticipating a relatively small or relatively large $V_T$ prior to termination of the inflation phase.

In patients who do not display much $V_T$ variability, the data, according to the random routine, fall in a limited volume range. The range can be expanded by reducing or increasing the level of PAV ventilation assist during breaths targeted for the inspiratory hold manoeuvre. Because the change in assist can be perceived by the patient long before the inspiratory hold occurs, and this may result in alterations in $P_{mus}$ during the hold, the reliability of this approach is inversely related to patient alertness. Since the absence of important $V_T$ variability is usually observed in less alert patients, there is some security in applying this procedure in patients with small $V_T$ variability. Further assurance can be obtained by asking the user (attendant) to input a rating of patient's level of alertness with the procedure being implemented only in patients deemed to have low vigilance.

In cases where $P_{aw}$ during the hold approaches but does not reach an asymptote before the minimum latency for behavioral responses (e.g. FIG. 2, Graph A), it may be useful to measure $P_{aw}$ at different points between 0 and minimum latency (e.g. 0 to about 300 msec of the inspiratory hold) and use a non-linear function to estimate the asymptote value. Such extrapolation, however, should preferably not be extended beyond an additional about 200 msec and be applied only when the $P_{aw}$ pattern during the first about 300 msec shows a clear tendency toward an asymptote (e.g. FIG. 2).

After collection of a suitable number of observations, old data points may be deleted as new ones are acquired, thereby resulting in a continuously updated pressure-volume relation. The results may be displayed in a graphic and/or numerical form. Some examples of graphic patterns are shown in FIG. 3. The entire data set might fit a linear function (FIG. 3, Graphs a, b, c). Conversely, the data may show relative stiffening in the high $V_T$ range while the linear range in lower $V_T$ range may extrapolate to PEEP or to a pressure above or below PEEP (FIG. 3, Graphs d, e, f). Other patterns are also possible. Such displays, and their mathematical counterparts, allow a comprehensive assessment of the pressure-volume relation that is continuously updated.

Although in most patients tested by the procedure of the present invention, the scatter of data points about the regression line is minimal and acceptable, there is, in some patients, substantial scatter reducing the confidence in the slope and intercept of the relation. The inventor has found that, when this occurs, it is often related to ventilatory variables preceding the breath selected for hold and these act to change the volume at the beginning of the selected breath. In other cases, the scatter is related to differences in inspiratory time of the breaths selected for the inspiratory hold. This occurs particularly in patients with pronounced viscoelastic behaviour. When scatter is excessive, ventilatory variables in breaths preceding the selected breaths (e.g. tidal volume, expiratory time, ventilation . . . etc) as well as inspiratory time of the occluded breaths are incorporated in the regression equation as co-variables. Such procedure invariably reduces the scatter and provides more confident estimates of elastic recoil at different points during inspiration.

Another cause of excessive scatter is the inclusion of faulty data. Such faulty data may occur, for example, when a cough or other erratic development occurs in the course of, or immediately before, the selected breaths. These faulty points may be identified, and deleted, by use of specified criteria including, but not limited to, patterns of flow, $P_{aw}$ and/or volume during or before the selected breaths being clearly outside the normal range of variability established in the particular patient being ventilated.

How to interpret the Results and to set the Volume Assist in the PAV ventilation mode:

i) The average $P_{hold}$ less PEEP is divided by the average $V_T$ to provide a single elastance value (or its reciprocal, compliance). VA can be set to the desired fraction of the single value. This would be clearly appropriate when the P-V relation is linear and with an intercept similar to PEEP (e.g. pattern "a", FIG. 3). This approach is not ideal where intercepts exist.

ii) The presence of a $P_{aw}$ intercept that is higher than PEEP (e.g. patterns b and e, FIG. 3) signifies either the presence of dynamic hyperinflation (DH) or a stiff respiratory system in the low volume range (e.g. abdominal distension, very small FRC, airway closure . . . etc). These two possibilities cannot be easily distinguished. Two approaches may be used to provide VA in this case:

a)

$$VA = I + f \cdot V/S$$

where I is the difference between pressure intercept and PEEP, S is the slope of the linear part of the PV curve, V is instantaneous volume, and f is the fraction of elastic load to be unloaded.

b) The lowest data range is connected to PEEP (dashed lines, patterns b and e, FIG. 3) and VA becomes a fraction (set by the user) of the pressure-volume relation defined by the dashed extrapolated segment and the regression line obtained from actual data. Where the actual data show stiffening in the upper $V_T$ range, it is desirable to extend the linear function upwards (graph e, FIG. 3), although non-linear functions that accommodate the upper stiffening may also be used.

iii) The presence of an intercept that is lower than PEEP signifies either that the breaths begin from a volume below passive FRC or that the entire data set is obtained in the stiff upper range of the P-V curve. In either case, it would be reasonable to connect the lowest actual data points to PEEP (dashed lines, graphs c and f, FIG. 3) and VA becomes a desired fraction of the relation defined by the dashed extrapolated line and the linear function obtained from the actual data.

iv) In all cases, suitable non-linear functions may be used.

2) Procedure for Automatic Determination of the Passive Pressure-Flow Relationship (Resistive Properties) (second aspect of invention):

Assessment of the resistive properties of the respiratory system in patients with spontaneous respiratory efforts on mechanical ventilation has been problematic and no satisfactory method currently exists. It is possible to estimate lung resistance using esophageal pressure measurement according to standard methods used in non-ventilated patients. This approach, however, is invasive and the results do not include chest wall resistance. It is also difficult to assess non-linearities in the pressure-flow relation using this technique, particularly in the pressure-support (PSV) and proportional assist (PAV) ventilation modes. For ventilation adjustment of the flow-assist gain of PAV ventilation, it is necessary to consider total respiratory resistance (i.e. not only lung resistance) and non-linearities should preferably also be taken into account.

The inspiratory hold technique, initially introduced for patients on controlled ventilation, has been used also in the assist modes and is currently the most commonly employed approach. This approach, however, is only possible when the patient is in the volume-cycled modes and cannot be applied in PSV or PAV. Furthermore, even in the volume-cycled mode there are problems related to time delays between peak flow and the point of zero flow, which can be as long as about 250 msec, Although in controlled ventilation, this delay can be corrected for, correction is not possible during assisted volume-cycled ventilation since during the delay period patient's effort ($P_{mus}$) could easily have changed, thereby invalidating the basic assumption of the method and producing erroneous results.

Oscillation techniques have been used extensively to measure resistance in non-ventilated humans and in ventilated paralyzed animals. Application of these techniques to mechanically ventilated patients in the assist modes has been hampered by numerous technical problems including non-linear behaviour of the pressure-flow and pressure-volume relations, varying background flow, volume and $P_{mus}$, which necessitate the use of high frequency oscillation so that the slower background changes can be filtered out (however resistance at high frequency is different from resistance at normal breathing frequency), the need to apply the oscillations for a relatively long time, with associated perception problems, which further complicates the analysis.

The present invention, according to this second aspect of the invention, circumvents the above problems using innovative procedures. Furthermore, it is non-invasive, that is not requiring any additional instrumentation of the patient, provides information about the entire pressure-flow relationship in the operating range, including any non-linearities that may exist, and can be easily automated. Although the procedure is suitable for all forms of mechanical ventilation, it is primarily intended for use with PAV ventilation in order to provide a continuously updated estimate of the resistive pressure-flow relationship that can be used to adjust the flow assist component of PAV ventilation.

Figure 4A:
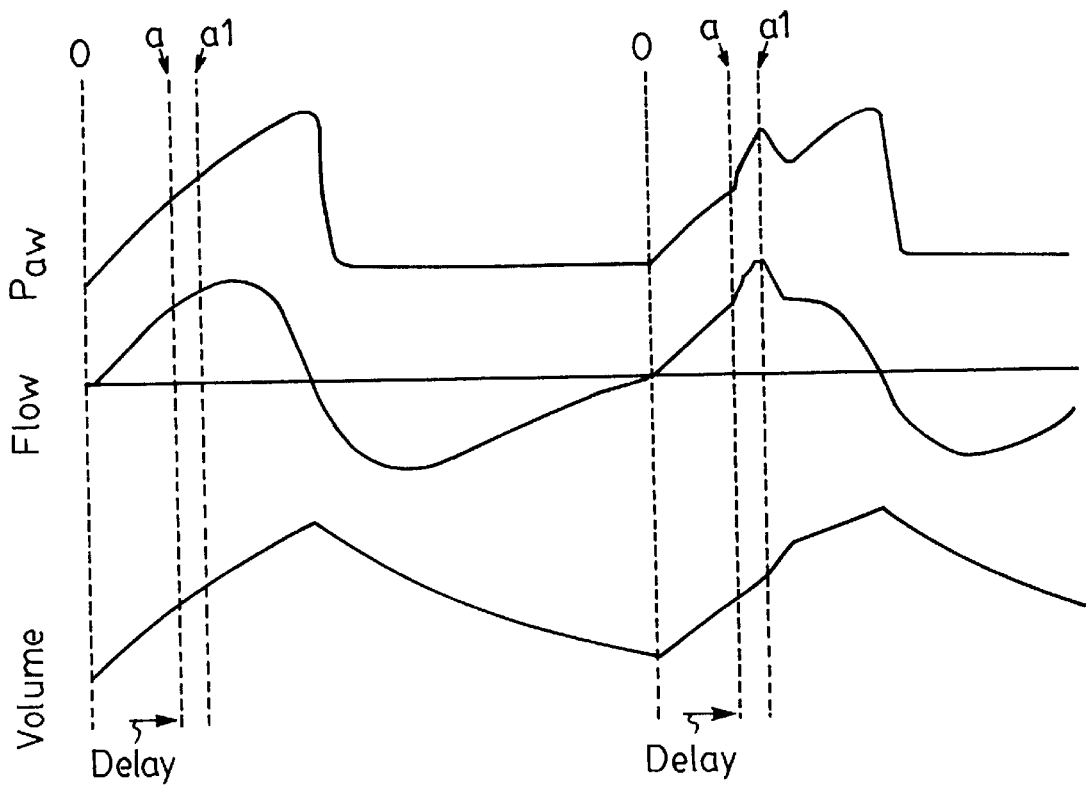
FIG. 4, which comprises graphs A and B, shows the plots of $P_{aw}$, Flow and Volume for positively perturbed (Graph A) and negatively perturbed (Graph B) breaths, in accordance with another embodiment of the invention.
Figure 4B:
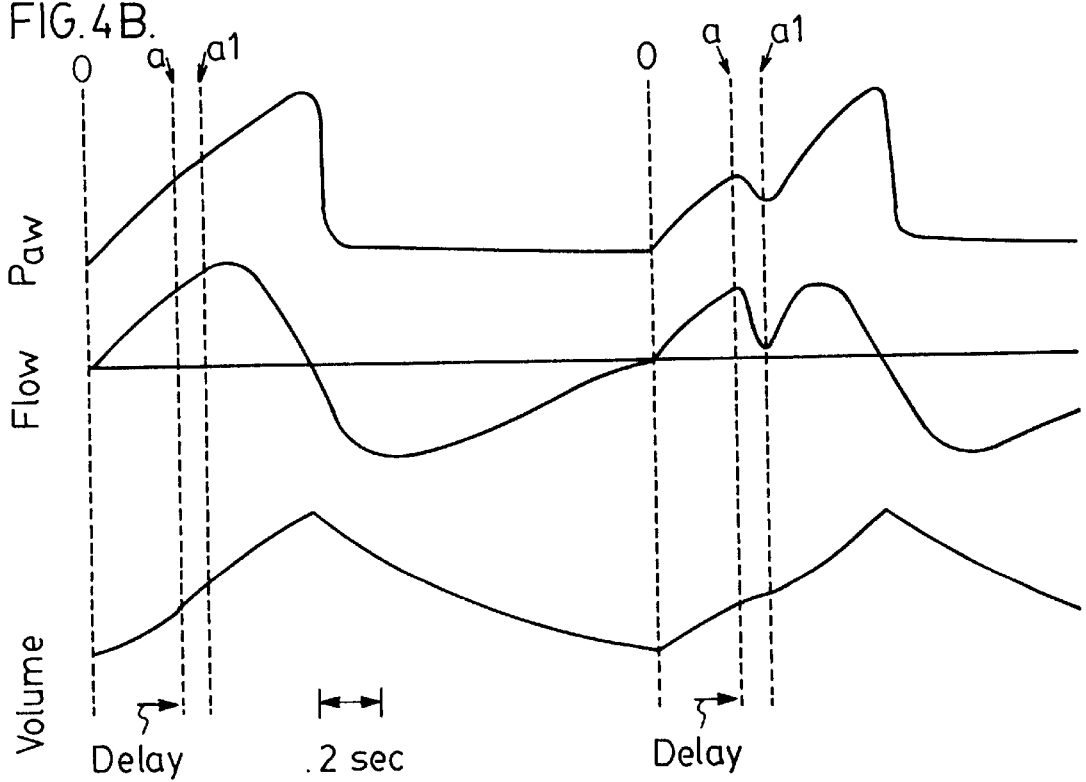

The features of the method of the present invention according to this second aspect of the invention, therefore, comprise the following:

a) applying brief mechanical perturbations in the course or ongoing inspiratory phases, said mechanical perturbation beginning at a specified time or flow after the onset of inspiratory phase with only one perturbation being applied in a given breath (e.g. see FIG. 4);

b) limiting the analysis of the consequences of these perturbations to a period that is less than the minimum latency for behavioural responses (preferably $\leq$ about 250 msec);

c) applying perturbations of at least two different amplitudes and/or polarity (i.e. different forms) with the amplitudes being selected to result in a flow range during the perturbations that spans the flow range encountered in unperturbed breaths. Thus, if perturbations are to be applied at a time when flow is naturally high, one may select negative perturbations of two or more amplitudes, with the amplitude of the largest negative perturbation being selected to reduce flow to near zero (e.g. FIG. 4B). Alternatively, if the perturbations are to be given at a point where flow is naturally close to zero, two or three positive perturbations may be used with the largest resulting in a flow that approximates the maximum flow observed in unperturbed breaths. If the perturbations are to be applied at a point where flow is intermediate, then a mix of positive and negative perturbations can be used to obtain the desired flow range;

d) measuring pressure ($P_{aw}$), flow ($\dot{V}$) and volume (V) at suitable intervals during the perturbation and storing the results;

e) averaging the results from multiple determinations with each type/amplitude of perturbation in order to eliminate the effect of random breath by breath variability in background conditions (for example, due to differences in $P_{mus}$ or volume at beginning of inspiration . . . etc) at the selected time of measurement. When a suitable number of observations per perturbation form is obtained, differences between average pressure, flow and volume among different perturbation forms can be reliably attributed to the perturbations themselves and not to different background conditions.

f) Pressure, flow and volume in unperturbed breaths may also be measured over an identical or similar time interval as the time of measurements in perturbed breaths (FIG. 4) and a suitable number of such observations is also averaged providing an additional set of data to define the non-linear pressure-flow relation. A minimum of two types of perturbations and the data from unperturbed breaths are needed to define the non-linear behaviour. Alternatively, data from unperturbed breaths can be replaced by one additional kind of perturbation. Thus, one may use positive perturbations of two different amplitudes and a negative perturbation or two different negative perturbations and one positive perturbation. Other permutations are clearly possible, the main intended result is to produce at least three sets of averaged data (for $P_{aw}$, $\dot{V}$ and V) in which flow covers a wide range.

g) Differences in average $P_{aw}$ between the different sets are related to the different flow and different volumes. Although these sets of results can be solved with standard mathematical methods to produce values for resistance and elastance, it is preferable to obtain values of elastance independently and allow for the impact of differences in volume on $P_{aw}$ in the data sets using these independently determined elastance values. This is because, in view of the brief nature of the perturbation and relatively small changes in flow, the differences in volume among different data sets in typically very small (e.g. FIG. 4). Elastances calculated from the data sets collected in accordance with the present invention may be erroneous in the presence of even minor noise.

Because the procedures for measuring elastic (procedure 1 above) and resistive properties (procedure 2 above) are intended to run concurrently, the elastance values obtained from procedure 1 can be used to estimate the elastic pressure associated with the difference in volume among data sets and, hence, to arrive at the pressure related to difference in flow ($P_{res}$) Thus, $$\Delta P_{res} = \Delta P_{aw} - \Delta V \cdot E$$

Where $\Delta P_{aw}$ is the difference in average $P_{aw}$ between two sets of observations, $\Delta V$ is the difference in volume between the two sets and E is the incremental elastance determined from procedure 1 or other suitable method. The value of $\Delta P_{res}$ so determined is attributed to the difference in flow between the two sets. In the presence of three or more sets spanning different flow ranges, it is possible, using standard mathematical techniques, to estimate with precision the pressure-flow relation over the entire relevant flow range, including any non-linearities.

The specific features of the procedure according to this aspect of the present invention which overcome prior art problems include:

a) Application of perturbations at a specific time into the inspiratory phase. This feature, after averaging of a number of observations, ensures that differences between variables measured during the perturbation are related to the perturbation and not to varying background conditions.

b) Limitation of analysis to a time within the latency for behavioural responses. This feature eliminates the confounding influence of these responses.

c) Because only one perturbation is applied in a given breath, and there is a time window of about 200 to 300 msec to apply it, the perturbation frequency content can be sufficiently low so that frequency dependence of resistance does not seriously affect results.

d) Because only one perturbation is made in a given breath and perturbations are applied infrequently, the amplitude of the flow perturbation can be relatively large. This feature is not feasible with conventional oscillation techniques where repetitive oscillations over relatively long periods are produced. The relatively largo amplitude of flow perturbations permits the determination of the pressure-flow relationship over the entire relevant range while causing little or no discomfort to the patient.

Thus, the present invention offers all the advantages of the conventional oscillation techniques while eliminating the difficulties associated with its implementation in this clinical setting and while remaining non-invasive, easily automated and permitting determination of non-linear behaviour over a wide flow range.

Preferred Procedure for Pressure-Flow Relationship:

Inspiratory flow to the patient ($\dot{V}$) and its integral, volume (V), along with airway pressure ($P_{aw}$) are continuously measured using standard techniques described in the prior art. These measurements can be effected with instrumentation resident in the ventilator or may be included in an external free-standing device. The signals are fed into a computer. Apart from its data acquisition capabilities, the computer is capable of sending out electric command signals (pulses) that are capable of altering $P_{aw}$ and/or $\dot{V}$ either by interfacing directly with the ventilator control system or by altering the output of an external mechanical system attached to the ventilator tubing.

Through suitable analytic algorithms, the computer determines the overage time, from onset of inspiration, at which flow is approximately in the midrange of its natural fluctuation. There follows a series of positive and negative perturbations of different amplitudes the intent of which is to determine the amplitude of positive output "pulses" required to increase flow to nearly the peak level usually reached in unperturbed breaths and amplitude of negative output "pulses" required to reduce flow to near zero when applied at the selected time. No more than one "pulse" is given per breath and, preferably, several breaths should separate any two perturbations.

Data collection begins once the time of delivery and amplitude of pulses is decided upon. At intervals, preferably random to avoid anticipatory responses in alert patients, the computer sends out a pulse (positive or negative in random or predetermined sequence) at the selected "delay" from the onset of inspiration ("delay", FIG. 4). $P_{aw}$, $\dot{V}$, V values are sampled immediately before the perturbation (e.g. lines a, FIG. 4) and at appropriate intervals during the period of the perturbation (e.g. every about 5 or about 10 msec for about 200 to 300 msec) Sampling is done at the same times in all types of perturbations and, also at the same times from onset of inspiration, in some unpertubated breaths (FIG. 4, left breaths). The different values are stored, being segregated according to variable ($P_{aw}$, $\dot{V}$, V) and perturbation type.

As new perturbations are made, more data are added to the tables and average values of $P_{aw}$, $\dot{V}$, and V are computed for all three conditions (unperturbed, positive perturbation, negative perturbation). The data points obtained immediately before the selected perturbation time in perturbed and unperturbed breaths (lines "a", FIG. 4) can be used to establish when an adequate number of observations has been collected. This would be when the average values for these initial data (lines "a", FIG. 4) obtained in perturbed and unperturbed breaths are very similar, thereby indicating that random breath by breath variability has been addressed by the number of samples gathered and the three sets of data started with similar conditions.

At this point there are three sets of average values related to positive perturbations (+), negative perturbations (−) and unperturbed (u) breaths. A variety of mathematical approaches can be used to extract the pressure-flow relationship from these averaged results. One simple approach is to define a single time during the perturbations that is at or close to peak flow in positive perturbations and at or close to nadir of flow in negative perturbations (e.g. lines "a1", FIG. 4). $P_{aw}$, $\dot{V}$ and V data at this time, obtained from positive and negative perturbations and from unperturbed breaths, are then used to compute two incremental resistances, IR(+) and IR(−), $$IR(+)=[P_{aw}(+)-P_{aw}(u)-\blacktriangle V(+)\times E]/[\dot{V}(+)-\dot{V}(u)]$$

where $P_{aw}(+)$ is the average $P_{aw}$ during the positive perturbation (as in line "a1", FIG. 4), $P_{aw}(u)$ is average $P_{aw}$ at the same time in unperturbed breaths, $\blacktriangle V$ is the difference in average volume between breaths with positive pulses at time "a1" (FIG. 4) and unperturbed breaths at the same time, E is incremental elastance determined from the concurrently operating procedure for determining elastance (procedure 1), $\dot{V}(+)$ is average flow at time "a1" in breaths with positive perturbations and $\dot{V}(u)$ is average flow in unperturbed breaths at the same time. IR(+) is incremental resistance between $\dot{V}(u)$ and $\dot{V}(+)$.

Likewise, incremental resistance for negative pulses (IR(−)) can be computed:

$$IR(-)=[P_{aw}(u)-P_{aw}(-)-\blacktriangle V(-)\times E]/[\dot{V}(u)-\dot{V}(-)]$$

where $P_{aw}(-)$ and $\dot{V}(-)$ are average $P_{aw}$ and $\dot{V}$, respectively, at time "a1" (FIG. 4) in breaths with negative perturbations and $\blacktriangle V(-)$ is the difference in average volume at time "a1" between unperturbed breaths and breaths with negative perturbations.

From IR(+) and IR(−), the constants $K_1$ and $K_2$ in Rohrer's equation ($P_{ras}=K_1\cdot\dot{V}+K_2\times\dot{V}^2$) can be computed. Thus, $$K_2=[IR(+)-IR(-)]/[\dot{V}(+)-\dot{V}(-)]$$

where $K_2$ is the constant related to turbulent flow, and $$K_1=IR(+)-K_2[\dot{V}(+)+\dot{V}(u)]$$

or, $$K_1=IR(-)-K_2[\dot{V}(-)+\dot{V}(u)]$$

where $X_1$ is the constant related to laminar flow.

In practice, after a suitable number of observations is collected and $K_1$ and $K_2$ are computed, the frequency of application of perturbations can be reduced. Old data can be deleted from the tables as new ones are added, so that the pressure-flow relation is continuously updated. Values for $K_1$ and $K_2$, obtained at different times during mechanical ventilation can be stored so as to allow the display of time-dependent trends in the pressure-flow relation.

Modifications to the above preferred procedure for establishing the pressure-flow relationship are possible. These include, but are not limited to:

a) Time of application of perturbation need not be in the flow midrange but can be at any time during inspiration. The type and amplitude of perturbations would have to be adjusted accordingly.

b) Perturbations may be applied at more than one selected time. In this case, however, data must be collected from unperturbed breaths or from other perturbations at each of the times selected for application of perturbations.

c) Clearly more than two types of perturbations can be applied. This would increase confidence in the values of $K_1$ and $K_2$ but would consume more time to arrive at a satisfactory solution.

d) Pertubations may be biphasic within the latency for behavioural responses. Likewise more than one biphasic perturbation can be included within this latency period. Although this may reduce the number of breaths that need to be perturbed to arrive at the pressure-flow relationship, the results may be affected by frequency dependence of resistance.

e) Data from unperturbed breaths may be omitted. In such case, however, it is necessary to have a minimum of three types of perturbation to establish the extent of non-linearity in the pressure flow relation.

f) Computation of IR values may be carried out before the baseline (initial) values (measured at lines "a", FIG. 4) had equalized in the different data sets. In such case the average values during perturbations need to be adjusted to reflect differences in initial conditions.

g) The actual method of causing a perturbation may vary. Some examples may include adding a transient positive or negative input to the basic control signal of the ventilator. Alternatively, particularly in the PAV mode of ventilation, perturbations can be produced by transient changes in the gain of the flow assist and/or volume assist. Perturbations can also be produced by mechanical devices that are independent of the main ventilator and which are connected to the tubing.

h) Individual breath data may be used to establish the pressure-flow relationship, in lieu of averaged data. This may be expected, however, to include considerable noise with less confidence in the resulting statistical function.

i) Other mathematical methods of data analysis may be used to arrive at the values of $K_1$ and $K_2$ in Rohrer's equation. Likewise, the data collected from procedures described in this application may be fitted to mathematical functions other than Rohrer's equation.

j) It is not entirely necessary to sample and store data from multiple points during each perturbation. Estimates of the pressure-flow relationship can be obtained if sampling is limited to one or two points in time during each perturbation provided that sampling time, relative to onset of perturbation, is approximately the same for all types of perturbation.

With both procedures (1 and 2 above) for the establishment of the passive pressure-volume relationship and of the passive pressure-flow relationship respectively, additional modifications (algorithms) can be added to identify and delete faulty data points from the collected data prior to computation of incremental resistances or of the pressure-volume relationship. Such faulty points may occur due to misapplied perturbations, occurrence of cough or other erratic developments during or before the breath. Such faulty nature may be established according to specified criteria including, but not limited to, patterns of $P_{aw}$, $\dot{V}$, and/or V during breaths used in analysis that are clearly outside the usual range of variability established from the majority of breaths in the patient being ventilated.

It may be desirable to store the parameters of the pressure-flow and pressure-volume relationship, obtained at different times in the course of mechanical ventilation, so that trends over time in these relations can be reviewed.

SUMMARY OF DISCLOSURE

In summary of this disclosure, the present invention provides a procedure for determining respiratory mechanics, including passive elastic and resistive properties, during assisted ventilation to provide improved patient ventilation. Modifications are possible within the scope of this invention.

What I claim is:

1. A method for estimating a passive pressure-volume relationship of a respiratory system in a patient on mechanical ventilatory support and producing spontaneous respiratory effort (assist mode of ventilation) to guide selection of a volume-assist component of a proportional assist ventilation mode (PAV), which comprises:

a) placing a ventilator in a proportional assist mode of ventilation, using empiric values of elastance and resistance, or values of elastance and resistance determined by other conventional methods, for initial adjustment of volume-related and flow-related assist components of the proportional assist ventilation mode, b) monitoring airway pressure ($P_{aw}$) and flow ($\dot{V}$) and volume (V) to the patient, c) holding flow at or near zero in selected breaths for a period beyond termination of a patient's inspiratory phase, d) measuring $P_{aw}$ at a point as far away as possible from the onset of an inspiratory hold but sooner than latency for a behavioral respiratory response to the inspiratory hold to provide $P_{hold}$, e) measuring the tidal volume ($V_T$) of the breaths selected for the inspiratory hold step, and f) establishing a relationship between $P_{hold}$ and $V_T$ in said selected breaths to provide a pressure-volume relationship over the $V_T$ range encountered during proportional assist ventilation to permit subsequent adjustment of a volume-related assist component for proportional assist ventilation.

2. The method of claim 1, including measuring said $P_{hold}$ at a time no greater than about 250 msec from the onset of an inspiratory hold.

3. The method of claim 1, including measuring said $P_{hold}$ at about 200 to about 250 msec from the onset of an inspiratory hold.

4. The method of claim 1, including using linear functions to fit the relationship between said $V_T$ and said $P_{hold}$.

5. The method of claim 1, including using non-linear functions to fit the relation between said $V_T$ and said $P_{hold}$.

6. The method of claim 1, including determining said $P_{hold}$ by non-linear extrapolation to an asymptote of multiple $P_{aw}$ values measured in the interval between onset of inspiratory hold and latency for a behavioral respiratory response to the inspiratory hold.

7. The method of any one of claims 1 to 6, including minimizing scatter around a fit between said $V_T$ and said $P_{hold}$ by including factors that can theoretically alter this relation in multiple regression analysis of said relation.

8. The method of claim 7 including selecting said factors from ventilation, $V_T$, expiratory time, expiratory flow and expiratory $P_{aw}$ in the interval preceding the breaths selected for inspiratory hold and/or inspiratory time of the selected breaths.

9. The method claimed in claim 1, including transiently increasing or decreasing the gain of volume-assist in PAV in said selected breaths to cause transient increase or decrease in $V_T$ to expand the range of $V_T$ over which the relation between $V_T$ and $P_{hold}$ is determined.

10. The method claimed in claim 1, including preferentially targeting breaths in which $V_T$ is predicted to be substantially larger or smaller than average $V_T$ for the inspiratory hold procedure in order to expand the range of $V_T$ over which the relation between $V_T$ and $P_{hold}$ is determined.

11. A method for estimating a passive pressure-flow relationship of the respiratory system in a patient on mechanical ventilatory support and producing spontaneous respiratory efforts (assist mode of ventilation) to guide selection of a flow-assist component in a proportional assist ventilation (PAV) mode, which comprises:
   a) placing a ventilator in a proportional assist ventilation mode using empiric values of elastance and resistance or values of elastance and resistance determined by other conventional methods, for initial adjustment of volume-related and flow-related assist components of the proportional assist ventilation mode,
   b) monitoring airway pressure ($P_{aw}$) and flow ($\dot{V}$) and volume (V) to the patient,
   c) applying brief perturbations in pressure, flow and volume of at least two different forms to selected breaths, such perturbations occurring at a predetermined time during the inspiratory phase of said selected breaths,
   d) determining the $P_{aw}$, flow ($\dot{V}$) and volume (V) at predetermined times during the perturbation less than latency for a behavioural respiratory response to the perturbation.
   e) determining the $P_{aw}$, $\dot{V}$ and V at similar times to those used in step (d) in unperturbed breaths,
   f) averaging results of a number of each form of perturbed and of unperturbed breaths, and
   g) utilizing the average values of $P_{aw}$, $\dot{V}$ and V obtained from the different forms of perturbed and from unperturbed breaths to provide a pressure-flow relationship to permit subsequent adjustment of the flow-related assist component for proportional assist ventilation.

12. The method of claim 11 including selecting said perturbation of at least two different forms from positive perturbations of two or more amplitudes, negative perturbations of two or more amplitudes, biphasic perturbations, and a mix of positive and negative perturbations.

13. The method of claim 11 wherein including determining said $P_{aw}$, $\dot{V}$ and V during the perturbation in less than about 200 msec.

14. The method of claim 11, including effecting step (g) by mathematically fitting the values determined in step (f) to Rohrer's equation:

$$P_{res} = \dot{V} \cdot K_1 + \dot{V}^2 \cdot K_2$$

where $P_{res}$ is resistive pressure and $K_1$ and $K_2$ are constants reflecting laminar and turbulent components of resistance, respectively.

15. The method of claim 11, including replacing observations in unperturbed breaths by one additional form of perturbation.

16. The method of claim 11, including applying perturbations when a specific flow is reached rather than a specific time into inspiration.

17. The method of claim 11, including basing determination of the pressure-flow relationship on differences between individual breath values within different forms of perturbations rather than values obtained from averages of individual breath values of perturbed and unperturbed breaths.

18. The method of claim 11, including using average values obtained from unperturbed breaths as reference for calculation of change in $P_{aw}$, $\dot{V}$ and V produced by the different forms of perturbation to result in average $\Delta P_{aw}$, $\Delta \dot{V}$ and V for each form of perturbation with the overall pressure-flow relationship being determined from said average differences.

19. The method of claim 18, including using said differences in $\Delta P_{aw}$, $\dot{V}$ and V to calculate two or more incremental resistance values.

20. The method of claim 11, including applying perturbations at more than one point in time into inspiration.

21. The method of claim 11, including producing the transient perturbations by deliberately increasing or decreasing the command signal that controls ventilator output in the PAV mode of ventilation by specified amounts, for a specified time, without changing the values of the flow-related and volume related assist of the PAV mode of ventilation.

22. The method of claim 11, including producing the transient perturbations by a transient change in the flow-related and/or volume-related assist gain of the PAV mode of ventilation.

23. The method of claim 11, including producing transient perturbations by a mechanical system, independent of the ventilator itself, and incorporated in the external tubing.

24. The method of claim 11, including applying the method during volume-cycled ventilation, rather than during PAV; by adding and/or subtracting specified amounts of flow for specified transients, to the ongoing programmed flow command routine.

25. The method of claim 11 including applying the method during modes of ventilation other than PAV and volume cycled assist, including CPAP mode, pressure support ventilation (PSV) or airway pressure release ventilation (APRV), whereby perturbations are produced by superimposing positive and/or negative transients to the usual control signal of the relevant mode.

26. The method of claim 1 or 11, including eliminating faulty data points from the analysis of the relation between $V_T$ and $P_{hold}$ or between pressure and flow, such faulty nature being established according to specified criteria including patterns of $P_{aw}$, $\dot{V}$ and/or V during breaths used in analysis, or during breaths preceding said breaths, that are outside the usual range of variability established from the majority of breaths in the patient being ventilated.

27. The method of claim 1 or 11, including extrapolating the pressure-volume and pressure-flow relationships beyond the range of actual observations.

28. The method of claim 1 or 11, including discarding old data points as new ones are collected in order to provide a continuous update of the pressure-volume and pressure-flow relationships.

29. The method of claim 1 or 11, including storing the pressure-volume and pressure-flow relationships computed at different times in the course of mechanical ventilation of a given patient for later display to provide time-related trends in such relationships.

30. The method of claim 1 or 11, including automating the procedures.

31. The method of claim 30, including automatically adjusting results of automated procedures to automatically adjust the volume-assist and/or flow-assist gains of the proportional assist ventilation.

* * * * *